United States Patent
Nakahara et al.

(10) Patent No.: US 6,191,113 B1
(45) Date of Patent: Feb. 20, 2001

(54) PEPTIDE FOR INHIBITING GROWTH OF SMOOTH MUSCLE CELLS

(75) Inventors: Yo Nakahara, Kumamoto-ken; Saburo Hara, Takatsuki; Yuichi Kamikubo; Sumiyo Takemoto, both of Kumamoto; Seiji Miyamoto, Kumamoto-ken, all of (JP)

(73) Assignee: Juridical Foundation The Chemo-Sero-Therapeutic Research Institute, Kumamoto-ken (JP)

( * ) Notice: Under 35 U.S.C. 154(b), the term of this patent shall be extended for 0 days.

(21) Appl. No.: 09/051,986

(22) PCT Filed: Oct. 23, 1996

(86) PCT No.: PCT/JP96/03080
  § 371 Date: Apr. 24, 1998
  § 102(e) Date: Apr. 24, 1998

(87) PCT Pub. No.: WO97/15598
  PCT Pub. Date: May 1, 1997

(30) Foreign Application Priority Data

Oct. 24, 1995 (JP) .................................... 7-300792

(51) Int. Cl.[7] .......................... A61K 38/10; A61K 38/17; C07K 7/08; C07K 14/47
(52) U.S. Cl. ................................ 514/13; 514/12; 514/14; 530/326
(58) Field of Search .................... 514/8, 13, 14, 514/17, 18, 19, 12; 530/300, 325, 326, 329, 330, 331, 350, 395

(56) References Cited

U.S. PATENT DOCUMENTS

| | | | |
|---|---|---|---|
| 5,254,536 | * 10/1993 | Racanelli et al. | 514/12 |
| 5,639,726 | * 6/1997 | Lawrence et al. | 514/12 |
| 5,772,629 | * 6/1998 | Kaplan | 604/52 |
| 5,824,644 | * 10/1998 | Abendschein | 514/12 |
| 5,849,702 | * 12/1998 | Garfinkel et al. | 514/12 |
| 5,981,471 | * 11/1999 | Papathanassiu et al. | 514/2 |

FOREIGN PATENT DOCUMENTS

| | | |
|---|---|---|
| 779774 | 3/1995 | (JP) . |
| 9124506 | 5/1997 | (JP) . |
| 9413811 | 6/1994 | (WO) . |
| WO 9604378 | 2/1996 | (WO) . |

OTHER PUBLICATIONS

XP–002123851, Derwent Publication Ltd., JP–08059698, Mar. 05, 1996.
XP–002123852, Derwent Publication Ltd., JP–09124506, May 13, 1997.
Ross, R., "The Pathogenesis of Atherosclerosis: a perspective for the 1900s," *Nature*, 362:801–809 (1993).
Landau, C. et al., "Percutaneous Transluminal Coronary Angioplasty," *The New England Journal of Medicine*, 330:981–993 (1994).

(List continued on next page.)

*Primary Examiner*—Jeffrey E. Russel
(74) *Attorney, Agent, or Firm*—Browdy and Neimark, PLLC

(57) ABSTRACT

A peptide comprising a peptide (A) of an amino acid sequence being abundant in basic amino acid residues and a peptide (B) of an amino acid sequence comprising at least two consecutive, hydrophobic amino acid residues wherein the peptide (B) is linked to the C-terminal of the peptide (A) directly or via several amino acid residues. The novel peptide of the present invention has the activity to inhibit growth of smooth muscle cells and a pharmaceutical composition comprising the peptide is useful for preventing or treating pathological conditions associated with growth of smooth muscle cells such as arteriosclerosis, restenosis after angioplasty, luminal stenosis after grafting blood vessel and smooth muscle sarcoma.

19 Claims, 4 Drawing Sheets

OTHER PUBLICATIONS

Hank, H. et al., "Time Course of Smooth Muscle Cell Proliferation in the Intima and Media of Arteries Following Experimental Angioplasty," *Circulation Research*, 67:651–659 (1990).

Ellis, S.G. et al., "Effect of 18– to 24–hour Heparin Administration for Prevention of Restenosis After Uncomplicated Coronary Angioplasty," *American Heart Journal*, 117:777–782 (1989).

Schwartz, L. et al., "Aspirin and Dipyridamole in the Prevention of Restenosis After Percutaneous Transluminal Cornory Angioplasty," *The New England Journal of Medicine*, 318:1714–1719 (1988).

Toshiya Shindo et al., Jinzo Zoki, 22, p. 459–461 (1993).

Bronze, G.J., "Isolation of the Tissue Factor Inhibitor Produced by HepG2 Hepatoma Cells," *Proc. Natl. Acad. Sci., USA*, 84:1886–1890 (1987).

Wun, T.–C. et al., "Cloning and Characterization of a cDNA Coding for the Lipoprotein–associated Coagulation Inhibitor Shows That it Consists of Three Tandem Kunitz–type Inhibitory Domains," *Journal of Biological Chemistry*, 263:6001–6004 (1988).

Kamei, S. et al., "Amino Acid Sequence and Inhibitory Activity of Rhesus Monkey Tissue Factor Pathway Inhibitor (TFPI): Comparison with Human TFPI," *J. Biochem*, 115:708–713 (1994).

Wesselchmidt, R. L. et al., "cDNA Sequence of Rabbit Lipoprotein–associated Coagulation Inhibitor," *Nucleic Acid Research*, 18–21:6440 (1990).

Warn–Cramer, B. J. et al., "cDNA Sequence of Rabbit Tissue Factor Pathway Inhibitor," *Nucleic Acids Research*, 20–13:3548 (1992).

Enjoji, K. et al., "cDNA Cloning and Expression of Rat Tissue Factor Pathway Inhibitor (TFPI)," *J. Biochem*, 111–5:681–687 (1992).

Enjoyoji, K. et al., "Effect of Heparin on the Inhibition of Factor Xa by Tissue Factor Pathway Inhibitor: A Segement, Gly121–Phe243, of the Third Kunitz Domain Is a Heparin––Binding Side," *Biochemistry*, 34:5725–5735 (1995).

* cited by examiner

PEPTIDE FOR INHIBITING GROWTH OF SMOOTH MUSCLE CELLS

TECHNICAL FIELD OF THE INVENTION

The present invention relates to a novel peptide which can inhibit growth of smooth muscle cells. The present invention also relates to a medicament for inhibiting growth of smooth muscle cells comprising said peptide.

BACKGROUND OF THE INVENTION

Smooth muscle cells are found in the media of aorta, the gastrointestinal tracts, the lung and the like. There are known diseases associated with extraordinary growth of smooth muscle cells, including arteriosclerosis, restenosis after angioplasty, luminal stenosis after grafting blood vessel, smooth muscle sarcoma and the like.

Arteriosclerosis is generally defined as a topical arterial lesion exhibiting intimal thickening, reconstruction, sclerosis or functional deterioration of the arterial wall and pathologically classified into three groups, i.e. micro-arteriosclerosis, calcification of the media and atherosclerosis. Among these three groups, atherosclerosis causes ischemic heart diseases, cerebral apoplexy or cerebral infarction and thus clinically most important. Atherosclerosis, when it occurred at the coronary artery, causes angina pectoris by narrowing the lumen, or leads to severe diseases such as unstable angina or myocardial infarction by forming thrombus in case of the rupture of atherosclerotic lesion. Atherosclerosis, when it occurred at the cerebral artery, also causes cerebral infarction or intracerebral bleeding, or leads to occlusive arteriosclerosis in case of the leg-governing arteries (from the aorta under the kidney to the common femoral artery). Thus, atherosclerosis is a cause of severe diseases.

As a mechanism of an onset of atherosclerosis, "Injury to Response" theory has widely been accepted today [Ross, R., Nature, 362, p801 (1993)]. That is, endothelial cells of blood vessel produce various growth factors which accelerate growth of smooth muscle cells when they are injured or given stimuli such as hyperlipidemia, viral infection or hypertension. As a result, smooth muscle cells grow to lead to intimal thickening.

For internally treating arteriosclerosis, a medicament for treating the risk factors such as an antihyperlipidemia or an antihypertensive has been administered, or a medicament for inhibiting the onset of arteriosclerosis such as an antioxidant, an antiplatelet, a vasodilator or an anticoagulant has been administered up till the present. However, these medicaments are not sufficiently effective in the clinical point of view.

For angina pectoris or myocardial infarction as caused by arteriosclerosis, some surgical treatments such as Percutaneous Transluminal Coronary Angioplasty, atherectomy, laser excision or stent implant have been employed and successful to some extent. Among these, Percutaneous Transluminal Coronary Angioplasty (PTCA) has widely been used to keep blood flow. PTCA has become popular soon as a radically curable means for treating angina pectoris and nowadays is one of established procedures for treating angina pectoris since it is more convenient than coronary artery bypass grafting (CABG), can easily be used repeatedly, and induces less postoperative complications even in the aged [Landau, C., N. Engl. J. Med., 330, p981 (1994)].

However, although there have been improvement of procedures or instruments or development of novel procedures in these PTCA and atherectomy angioplasties, a crucial problem still remains unsettled, i.e. restenosis is observed in 25 to 49% of those patients operated three to five months after operation. Since restenosis requires further treatment such as PTCA or CABG, it is a quite serious problem in view of burden to patients or financial difficulties of insurance. Although various drugs have been administered for the purpose of inhibiting the onset of restenosis, they are not sufficiently effective.

A mechanism of the onset of restenosis has been studied. Recent studies show that a cause of restenosis is growth of smooth muscle cells at the intima of blood vessel [Hanke, H. et al., Circulation Res., 67, p651 (1990)]. That is, it is estimated that restenosis is caused by growth of smooth muscle cells in blood vessel which occurred to repair the structure of blood vessel physically destroyed by, for example, balloon catheter but unrestrictedly proceeded. Thus, there has been an attempt to treat restenosis by inhibiting growth of smooth muscle cells at the restenosed site, including a clinical test with heparin [Ellis, S. G. et al., Am. Heart J., 117, p777 (1989)], a clinical test with a combination of aspirin and dipyridamole [Schwartz, L. et al., N. Engl. J. Med., 318, p1714 (1988)], and the like. However, none of these could effectively inhibit restenosis.

Furthermore, in addition to coronary angioplasty as mentioned above, an operation of grafting self blood vessel from other portions (internal thoracic artery, gastroepiploic artery, and great saphenous vein are mainly used), i.e. coronary artery bypass, has clinically been used to reconstruct blood flow for coronary artery where excess stenosis or occlusion has occurred as a cause of ischemic heart diseases. However, even in coronary artery bypass, intimal thickening of the grafted blood vessel frequently occurs to stenose the lumen of said grafted vessel to interrupt blood flow, and hence, it is not clinically reliable. It was reported that growth of smooth muscle cells and production of extracellular matrix associated therewith plays a central role in such intimal thickening [Toshinobu Horie, Nippon Rinsho, 52, p1010 (1994)], and thus, patency of the graft for a long period of time is expected by inhibiting growth of smooth muscle cells. In addition, not limited to coronary artery, graft of self blood vessel for the injured ones is commonly employed in case of surgical injury of extremities in the field of plastic surgery. It is known that luminal stenosis caused by growth of smooth muscle cells frequently occurs particularly at the anastomotic sites with normal blood vessel.

In case of grafting blood vessel, an artificially prepared blood vessel (hereinafter referred to as "artificial vessel") is also used for the graft in place of self blood vessel from other portions. The artificial vessel is used not only for coronary artery but also for other vessels, including for example, for injured blood vessel after amputation of extremities, as blood vessel for AV shunt in patients with artificial dialysis, and the like. However, even in case of an artificial vessel, it is also known that intimal thickening frequently occurs at the anastomotic site with normal blood vessel to interrupt blood flow [Toshiya Shindo et al., Jinko Zoki, 22, p459 (1993)]. For both self blood vessel and an artificial vessel, a drug which can effectively inhibit growth of smooth muscle cells has not yet been found and thus there is a desire to develop such drug.

Smooth muscle sarcoma, smooth muscle cells-derived malignant tumor, mainly appears at the uterus and the gastrointestinal tract as well as the posterior peritoneum and the subcutaneous soft tissue, grows destructively and invasively, and usually metastasizes to the lung through blood circulation. Smooth muscle sarcoma has been treated by surgical excision in combination with administration of a usual anti-cancer agent. However, a usual anti-cancer agent exhibits unacceptable side effects, and hence, there is a desire to develop a drug which can specifically inhibit growth of smooth muscle cells.

DISCLOSURE OF THE INVENTION

Under the circumstances, in order to find out a substance which can effectively inhibit arteriosclerosis and restenosis after Percutaneous Transluminal Coronary Angioplasty or other angioplasties, the present inventors have searched for an accelerating factor and an inhibiting factor for restenosis using a model animal for intimal thickening of blood vessel prepared by balloon injury and a culture of blood vessel smooth muscle cells. As a result, the present inventors have already found that a tissue factor pathway inhibitor (TFPI) exhibited a quite novel activity to inhibit growth of smooth muscle cells (Japanese patent application No. 245548/1995).

TFPI is a glycoprotein known to inhibit extrinsic blood coagulation [Broze, G. J., Proc. Natl. Acad. Sci. USA, 84, p1886 (1987)]. TFPI has a protein structure where three regions called generally "Kunitz" (from the amino terminal, referred to as "Kunitz 1", "Kunitz 2" and "Kunitz 3") are present in series, to which carboxyl terminal a region being abundant in basic amino acids (hereinafter referred to as "C-terminal region") is linked. Kunitz 1 binds to activated Factor VII, one of blood coagulation factors, to neutralize the protease activity of said factor. Kunitz 2 binds to activated Factor X, also one of blood coagulation factors, to neutralize the protease activity of said factor. Through these activities, TFPI is considered to effectively inhibit blood coagulation at its early stage. The C-terminal region is known to bind to glycosaminoglycan with a negative charge, especially heparin. Human TFPI consists of 276 amino acid residues and has a molecular weight of about 42,000.

The present inventors further investigated the activity of TFPI to inhibit growth of smooth muscle cells. As a result, the present inventors have found that the C-terminal region of TFPI is responsible for the activity to inhibit growth of smooth muscle cells viewing that (i) TFPI lacking the C-terminal region does not exhibit the inhibitory activity, and (ii) a synthetic peptide having a similar amino acid sequence to that of the C-terminal region exhibits the activity strongly. The present inventors further investigated a homologous peptide to the C-terminal region, and as a result, have found that a peptide, which comprises a peptide (A) of an amino acid sequence being abundant in basic amino acid residues and a peptide (B) of an amino acid sequence comprising at least two consecutive, hydrophobic amino acid residues wherein the peptide (B) is linked to the carboxyl terminal of the peptide (A) directly or via several amino acid residues, has the activity to inhibit growth of smooth muscle cells, and thus the present invention has been completed.

That is, an object of the present invention is to provide a novel pharmaceutical composition for inhibiting growth of smooth muscle cells comprising said peptide as an active ingredient.

Another object of the present invention is to provide a medicament which can effectively prevent or treat arteriosclerosis associated with growth of smooth muscle cells, restenosis after Percutaneous Transluminal Coronary Angioplasty or other angioplasties, luminal stenosis after grafting blood vessel, and smooth muscle sarcoma.

BEST MODE FOR CARRYING OUT THE INVENTION

Figure 1:
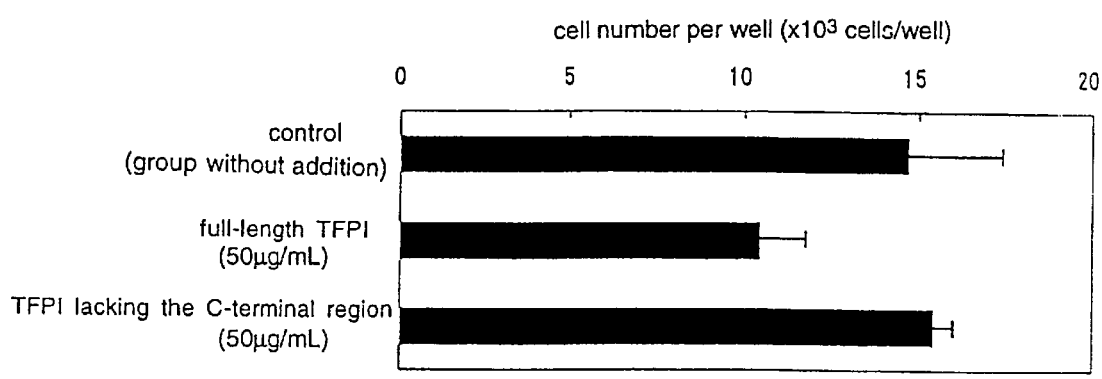
FIG. 1 shows the activity to inhibit growth of smooth muscle cells with addition of a full length TFPI or TFPI lacking the C-terminal region.

The peptide of the present invention is a peptide comprising a peptide (A) of an amino acid sequence being abundant in basic amino acid residues and a peptide (B) of an amino acid sequence comprising at least two consecutive, hydrophobic amino acid residues wherein the peptide (B) is linked to the C-terminal of the peptide (A) directly or via several amino acid residues.

A basic amino acid which can be used in the peptide (A) includes lysine (also referred to as "Lys" or "K"), arginine (also referred to as "Arg" or "R") or histidine (also referred to as "His" or "H"). As to the number of a basic amino acid which can be used in the peptide (A), at least four basic amino acids should be contained when the peptide (A) comprises, for example, thirteen amino acid residues. Such a peptide comprising thirteen amino acid residues has a quite excellent activity to inhibit growth of smooth muscle cells when it contains nine basic amino acid residues.

The peptide (A) comprising nine basic amino acid residues in a sequence of thirteen amino acid residues includes a peptide of an amino acid sequence: Ba1-Xa1-Ba2-Ba3-Ba4-Ba5-Ba6-Ba7-Xa2-Ba8-Xa3-Ba9-Xa4 (SEQ ID NO:21) wherein Ba1, Ba2, Ba3, Ba4, Ba5, Ba6, Ba7, Ba8 and Ba9 are basic amino acids each selected from Lys, Arg or His; Xa1, Xa2, Xa3 and Xa4 are any amino acid. Specifically, such a peptide includes a peptide of an amino acid sequence: Lys-Xa1-Lys-Arg-Lys-Arg-Lys-Lys-Xa2-Arg-Xa3-Lys-Xa4 (SEQ ID NO:22). More specifically, such a peptide includes a peptide of an amino acid sequence: Lys-Thr-Lys-Arg-Lys-Arg-Lys-Lys-Gln-Arg-Val-Lys-Ile (Amino acids 1–12 of SEQ ID NO:10).

A hydrophobic amino acid which can be used in the peptide (B) includes phenylalanine (also referred to as "Phe" or "F"), isoleucine (also referred to as "Ile" or "I"), leucine (also referred to as "Leu" or "L"), methionine (also referred to as "Met" or "M"), proline (also referred to as "Pro" or "P"), valine (also referred to as "Val" or "V"), tryptophan (also referred to as "Trp" or "W") and tyrosine (also referred to as "Tyr" or "Y").

The peptide (B) may be any peptide as far as it comprises at least two consecutive, hydrophobic amino acid residues. Preferably, the peptide (B) comprises "Ile-Phe". In case of three hydrophobic amino acid residues, the peptide (B) preferably comprises "Ile-Phe-Val".

The peptide (B) includes, for example, a peptide of an amino acid sequence: Ile-Phe-Val-Xaa (SEQ ID NO:23); a peptide of an amino acid sequence: Ile-Phe-Val-Xaa-Asn (SEQ ID NO:24); and a peptide of an amino acid sequence: Ile-Phe-Val-Xaa-Asn-Met (SEQ ID NO:25) wherein Xaa is either Lys or Gln.

The peptide of the present invention includes a peptide of an amino acid sequence which corresponds to the C-terminal region of tissue factor pathway inhibitor (TFPI). The C-terminal region generally encompasses a region situated C-terminal to Kunitz 3 (not inclusive) being abundant in basic amino acid residues and comprises up to thirty seven amino acid residues from the C-terminal of human or rabbit TFPI or up to thirty amino acid residues from the C-terminal of rat TFPI. The peptide of the present invention also encompasses a homologue of such C-terminal region wherein deletion, substitution, insertion or addition may be occurred at any of amino acid residues in the C-terminal region of TFPI.

An amino acid sequence of TFPI has been reported for human [Wun, T.-C. et al., J. Biol. Chem., 263, p6001 (1988)], for monkey [Kamei, S. et al., J. Biochem., 115, p708 (1994)], rabbit [Wesselschmidt, R. L. et al., Nuc. Acids Res., 18, p6440 (1990); Warn-Cramer, B. J. et al., Nuc. Acids Res., 20, p3642 (1992)], rat [Enjyoji, K. et al., J. Biochem., 111, p681 (1992)] and the like. The C-terminal region peptide of the present invention for administering to human should be prepared based on an amino acid sequence of human TFPI to minimize an immunological rejection and to attain sufficient efficacy.

The C-terminal region peptide of the present invention includes a peptide having a sequence of twenty three amino acid residues: KTKRKRKKQRVKIAYEEIFVKNM (SEQ ID NO:1) wherein N is asparagine (Asn); E is glutamic acid (Glu); Q is glutamine (Gln); A is alanine (Ala); V is valine (Val); M is methionine (Met); I is isoleucine (Ile); F is phenylalanine (Phe); K is lysine (Lys); R is arginine (Arg); T is threonine (Thr); and Y is tyrosine (Tyr) (Peptide 1; SEQ ID NO: 1), which corresponds to the amino acid residues from No. 254 (lysine) to No. 276 (methionine) of human TFPI.

The C-terminal region peptide of the present invention also includes a peptide having a sequence of twenty four amino acid residues: IKTKRKRKKQRVKIAYEEIFVKNM (Peptide 20; SEQ ID NO: 20), which corresponds to the amino acid residues from No. 253 (isoleucine) to No. 276 (methionine) of human TFPI.

A peptide of an amino acid sequence: KTKRKRKKQRVKIAYEEIFVQNM (Peptide 5; SEQ ID NO: 5) which is prepared by substituting the 3rd Lys from the C-terminal of Peptide 1 with Gln (glutamine) has more excellent activity to inhibit growth of smooth muscle cells than that of Peptide 1.

A pharmaceutical composition comprising the peptide having the activity to inhibit growth of smooth muscle cells of the present invention can be used as a medicament for treating or preventing pathological conditions associated with growth of smooth muscle cells, such as arteriosclerosis, restenosis after angioplasty, luminal stenosis after grafting blood vessel, and smooth muscle sarcoma. The angioplasty includes Percutaneous Transluminal Coronary Angioplasty, atherectomy, laser excision, stent implant and the like.

For improving the efficacy of a pharmaceutical composition comprising the peptide of the present invention, such as for obtaining a prolonged half-life within the living body, or for improving the absorption or topical concentration at an injured site, the present invention encompasses a composition comprising a homologue of the peptide with a partial chemical modification, specifically, chemical modification of the amino group at the amino terminal (N-terminal) or the carboxyl group at the C-terminal, or with addition of or in admixture with a sugar or a lipid, or a fusion with other compound or protein.

The peptide of the present invention may be prepared by any procedure, for example, by a chemical synthesis or by a genetic recombination technique. Alternatively, the peptide of the present invention may also be obtained by digestion of TFPI, which is purified from natural plasma or prepared by a genetic recombination technique, with some chemical treatment or with an appropriate protease.

In order to keep the efficacy of a pharmaceutical composition comprising the peptide of the present invention to the maximum, it should be sealed up and stored as a dry state by lyophilization wherein the composition may further comprise the conventional excipients or additives as suited.

A pharmaceutical composition comprising the peptide of the present invention may further comprise other drugs such as antihyperlipidemia, an antihypertensive, an antioxidant, an antiplatelet, a vasodilator or an anticoagulant as far as safety of the drug is confirmed.

A pharmaceutical composition comprising the peptide of the present invention may be formulated into suitable dosage forms together with a pharmaceutically acceptable carrier and administered directly into the lesion of blood vessel via a drug delivery catheter, coated on the surface of stent or balloon which is then administered to the lesion of blood vessel, or introduced into the vein or artery as a bolus or continuously. Alternatively, a pharmaceutical composition comprising the peptide of the present invention may be administered directly to the lesion as a powder without solubilization, or may be coated on a vasodilating instrument such as stent or balloon as a dry powder. As an alternative, a pharmaceutical composition comprising the peptide of the present invention may be administered orally as a liquid state or solid state. As a further alternative, a pharmaceutical composition comprising the peptide of the present invention may be administered in such a manner that a gene coding for the peptide of the present invention, which is incorporated into a suitable expression vector, is directly introduced into the lesion of smooth muscle cells to induce excess expression of the peptide in said lesion.

The present invention is illustrated in more detail by means of the following Examples to bring about a better understanding of the present invention, but should not be construed to be limited thereto.

EXAMPLE

Example 1

Preparation of Full-length TFPI and TFPI Lacking the C-terminal Region

TFPI used in this Example was purified from a culture supernatant of Chinese hamster ovary cell line into which cDNA encoding human TFPI was incorporated by an affinity chromatography using an anti-TFPI monoclonal antibody (HTFPIK9 (BIKOKEN KINKI14467)) conjugated gel and a heparin gel (Pharmacia-LKB) as described by Kamei et al. (Japanese patent application No. 188746/1993) or by Enjyoji et al. [Biochemistry, 34, p5725 (1995)]. A supernatant contained both full-length TFPI and TFPI lacking the C-terminal region, which could be separated from each other by an affinity chromatography with heparin gel followed by elution with a linear gradient of NaCl wherein TFPI lacking the C-terminal region is eluted at 0.4 to 0.5 mol/l of NaCl whereas full-length TFPI is eluted at 0.8 to 0.9 mol/l of NaCl. The thus obtained full-length TFPI was confirmed to be an intact TFPI molecule whereas the TFPI lacking the C-terminal region was confirmed to be a product after cleavage at the peptide bonding between the amino acid residue No. 249, Lys, and the amino acid residue No. 250, Gly, i.e. TFPI which is defective of a peptide of twenty seven amino acid residues from the C-terminal of TFPI, as determined by an amino acid sequencing or SDS-PAGE analysis.

Example 2

Involvement of C-terminal Region of TFPI in Activity to Inhibit Growth of Smooth Muscle Cells Vascular smooth muscle cells from human aorta (purchased from Kurabo K.K.) were used and subjected to passage culture with Dulbecco modified Eagle medium (hereinafter referred to as "DME") supplemented with 10% fetal calf serum. The smooth muscle cells with six passages were used in the following experiment.

The smooth muscle cells suspended in DME were plated on a 48 well culture plate (manufactured by Iwaki Glass K.K.) at a cell density of 5,000 cells/well and incubated in $CO_2$ incubator at 37° C. Two days after plating, the culture medium was exchanged with DME containing 50 μg/ml of full-length TFPI or 50 μg/ml of TFPI lacking the C-terminal region or with DME alone as a control and culture was continued in $CO_2$ incubator at 37° C. while the culture medium was exchanged with a fresh medium on every 2 days. The culture medium was used at 0.3 ml/well. Nine days after plating, the cells attached to the plate were detached by treatment with a trypsin/EDTA solution and then a cell number per well was counted with a hemocytometer. FIG. 1 is a graph showing a mean cell number as well as a standard deviation for three wells in each group. The group with addition of full-length TFPI had a significantly decreased cell number (Student's t-test: $p<0.05$) as compared to the control group, demonstrating the effect to inhibit growth of smooth muscle cells. On the contrary, TFPI lacking the C-terminal region did not exhibit this effect, and thus, it was shown that the C-terminal region of TFPI was necessary for inhibiting growth of smooth muscle cells. The full-length TFPI was tested for its toxicity with Cytotox 96 kit for measuring cellular toxicity (manufactured by Promega), and as a result, it was found that the full-length TFPI did not exhibit cellular toxicity, indicating that the effect to inhibit growth of smooth muscle cells was not exerted through cellular toxicity.

Example 3

Preparation of C-terminal Region Peptide from Human TFPI

In order to investigate the activity to inhibit growth of smooth muscle cells of a peptide corresponding to the C-terminal region of TFPI and a homologue thereof, the following peptides were prepared:

Peptide 1: a peptide having a sequence of twenty three amino acid residues: KTKRKRKKQRVKIAYEE-IFVKNM (SEQ ID NO: 1), which corresponds to the amino acid residues from No. 254 (lysine) to No. 276 (methionine) of human TFPI;

Peptide 2: a peptide having a sequence of eleven amino acid residues: KTKRKRKKQRV (SEQ ID NO: 2), which corresponds to the amino acid residues from No. 254 (lysine) to No. 264 (valine) of human TFPI;

Peptide 3: a peptide having a sequence of twelve amino acid residues: KIAYEEIFVKNM (SEQ ID NO: 3), which corresponds to the amino acid residues from No. 265 (lysine) to No. 276 (methionine) of human TFPI.

Furthermore, the following peptides were prepared which were a modified Peptide 1 having deletion, substitution, insertion or addition:

Peptide 4: IFVKNMAYEEKTKRKRKKQRVKI (SEQ ID NO: 4);

Peptide 5: KTKRKRKKQRVKIAYEEIFVQNM(SEQ ID NO: 5);

Peptide 6: KTKRKRKKQRVKIAYEELLLKNL (SEQ ID NO: 6);

Peptide 7: KTKRKRKKQRVKIIFVKNM (SEQ ID NO: 7);

Peptide 8: KTKRKRKKQRVKIAYOOIFVKNM (SEQ ID NO: 8);

Peptide 9: KTKRKRKKQRVKISFEEIFVKNM (SEQ ID NO: 9);

Peptide 10: LYKKIIKKLLESIAYEEIFVKNM (SEQ ID NO: 10);

Peptide 11: IKTKRKRKKQ (SEQ ID NO: 11);

Peptide 12: IKTKRKRKKQRV (SEQ ID NO: 12);

Peptide 13: IKTKRKRKKQRVKI (SEQ ID NO: 13);

Peptide 14: IKTKRKRKKQRVKIAYEE (SEQ ID NO: 14);

Peptide 15: IKTKRKRKKQRVKIAYEEI (SEQ ID NO: 15);

Peptide 16: IKTKRKRKKQRVKIAYEEIF (SEQ ID NO: 16);

Peptide 17: IKTKRKRKKQRVKIAYEEIFV (SEQ ID NO: 17);

Peptide 18: IKTKRKRKKQRVKIAYEEIFVK (SEQ ID NO: 18);

Peptide 19: IKTKRKRKKQRVKIAYEEIFVKN (SEQ ID NO: 19); and

Peptide 20: IKTKRKRKKQRVKIAYEEIFVKNM (SEQ ID NO: 20)

wherein A is alanine (Ala); E is glutamic acid (Glu); F is phenylalanine (Phe); I is isoleucine (Ile); K is lysine (Lys); L is leucine (Leu); M is methionine (Met); N is asparagine (Asn); Q is glutamine (Gln); R is arginine (Arg); S is serine (Ser); T is threonine (Thr); V is valine (Val); and Y is tyrosine (Tyr).

These peptides were chemically synthesized by Fast-Moc™ solid phase synthesis using 431A Peptide Synthesizer (manufactured by Perkin Elmer Japan Applied Biosystems) in accordance with the protocol of this device. For example, Peptides 1 and 3 or Peptide 2 were synthesized from 0.25 mmol of Fmoc-L-Met-resin or 0.25 mmol of Fmoc-L-Val-resin (both manufactured by Perkin Elmer Japan Applied Biosystems), respectively, which were elongated by adding an amino acid one by one to the N-terminal. The same procedures were applied for synthesis of the other peptides. The amino acid monomer used in the elongation reaction was each 1 mmol of Fmoc-protected amino acid (manufactured by Perkin Elmer Japan Applied Biosystems). The thus synthesized peptides were deprotected and cleaved from the resin as described in the protocol "Introduction to Cleavage Techniques" of Perkin Elmer Japan Applied Biosystems.

The peptides were then extracted with distilled water from the crude crystals obtained after deprotection and cleavage from the resin and lyophilized to give crude peptides, which were purified by Brownlee reversed phase column (diameter 10 mm, length 250 mm; Perkin Elmer Japan Applied Biosystems) with a concentration gradient (0 to 100%) of 0.1% trifluoroacetic acid solution and 70% acetonitrile containing 0.09% trifluoroacetic acid.

Example 4

Figure 2:
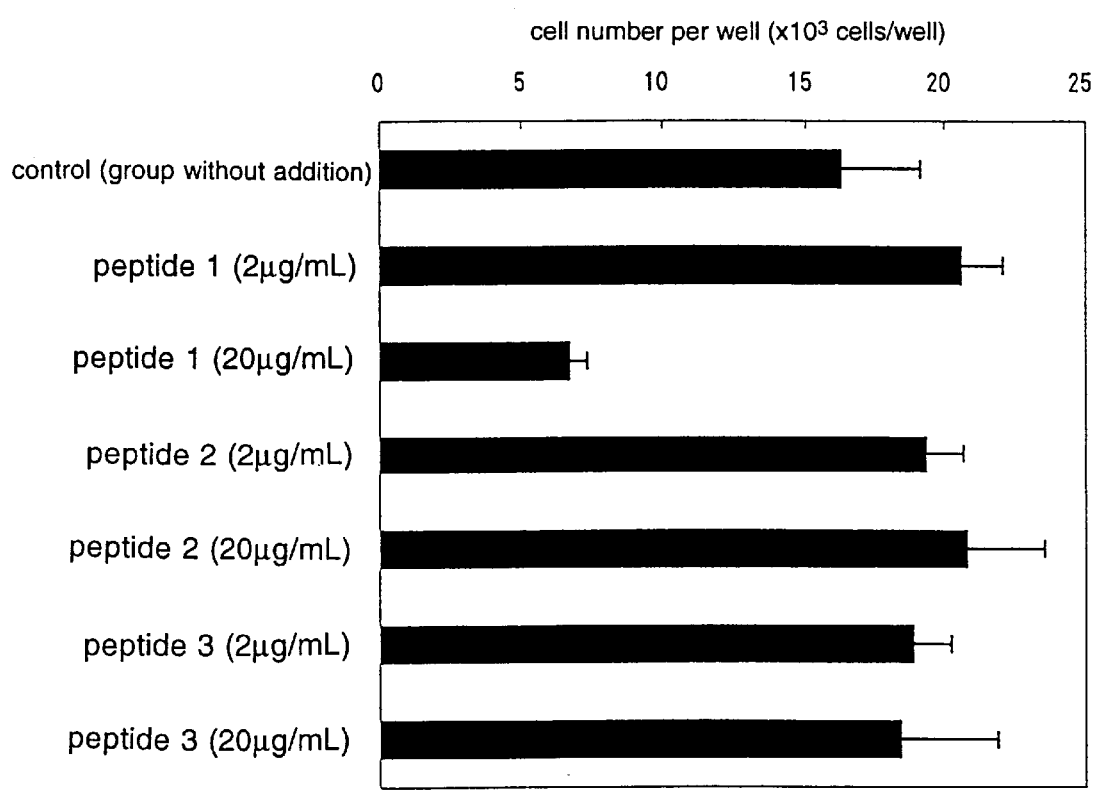
FIG. 2 shows the activity to inhibit growth of smooth muscle cells with addition of three peptides corresponding to the C-terminal region of TFPI wherein Peptide 1 has a sequence of twenty three amino acid residues: KTKRKRKKQRVKIAYEEIFVKNM (SEQ ID NO:1) which corresponds to the amino acid residues from No. 254 (lysine) to No. 276 (methionine) of human TFPI; Peptide 2 has a sequence of eleven amino acid residues: KTKRKRKKQRV (SEQ ID NO:2) which corresponds to the amino acid residues from No. 254 (lysine) to No. 264 (valine) of human TFPI; and Peptide 3 has a sequence of twelve amino acid residues: KIAYEEIFVKNM (SEQ ID NO:3) which corresponds to the amino acid residues from No. 265 (lysine) to No. 276 (methionine) of human TFPI.

Activity to Inhibit Growth of Smooth Muscle Cells by C-terminal Region Peptides of Human TFPI The cells were inoculated as in Example 2. Two days after inoculation, the culture medium was exchanged with DME containing respective concentration of the C-terminal region peptides and the cells were cultured in $CO_2$ incubator at 37° C. while exchanging the culture medium with the DME for every 2 days. The culture medium was used at 0.3 ml/well and DME alone was used as a control. Nine days after inoculation, a cell number per well was counted as in Example 2. FIG. 2 is a graph showing a mean value and standard deviation of a cell number for each group comprising 3 wells. The group added with 20 μg/ml of Peptide 1, which corresponds to twenty three amino acid residues in the C-terminal region of human TFPI, exhibited significant decrease in cell number as compared to the control group (Student's t-test; $p<0.05$). Thus, it was confirmed that Peptide 1 alone could be an effective agent for inhibiting growth of smooth muscle cells.

On the contrary, no activity to inhibit growth of smooth muscle cells was found for Peptide 2, which corresponds to eleven amino acid residues in the N-terminal region of Peptide 1, or Peptide 3, which corresponds to twelve amino acid residues in the C-terminal region of Peptide 1, even if they were added at 20 μg/ml. From these, it was estimated that both an amino acid sequence of Peptide 2 or a portion thereof and an amino acid sequence of Peptide 3 or a portion thereof should be present in a single molecule for exerting the activity to inhibit growth of smooth muscle cells.

Example 5

Activity to Inhibit Growth of Smooth Muscle Cells Exerted by Peptide 1 in a Concentration Dependent Manner Vascular smooth muscle cells of blood vessel from human aorta (purchased from Kurabo K.K.) were used. The culture medium was Humedia-SG (manufactured by Kurabo K.K.) containing a basic fibroblast growth factor (bFGF), an epidermal growth factor (EGF), insulin, and 5% fetal calf serum. The smooth muscle cells with six passages were used in the following experiment.

Figure 3:
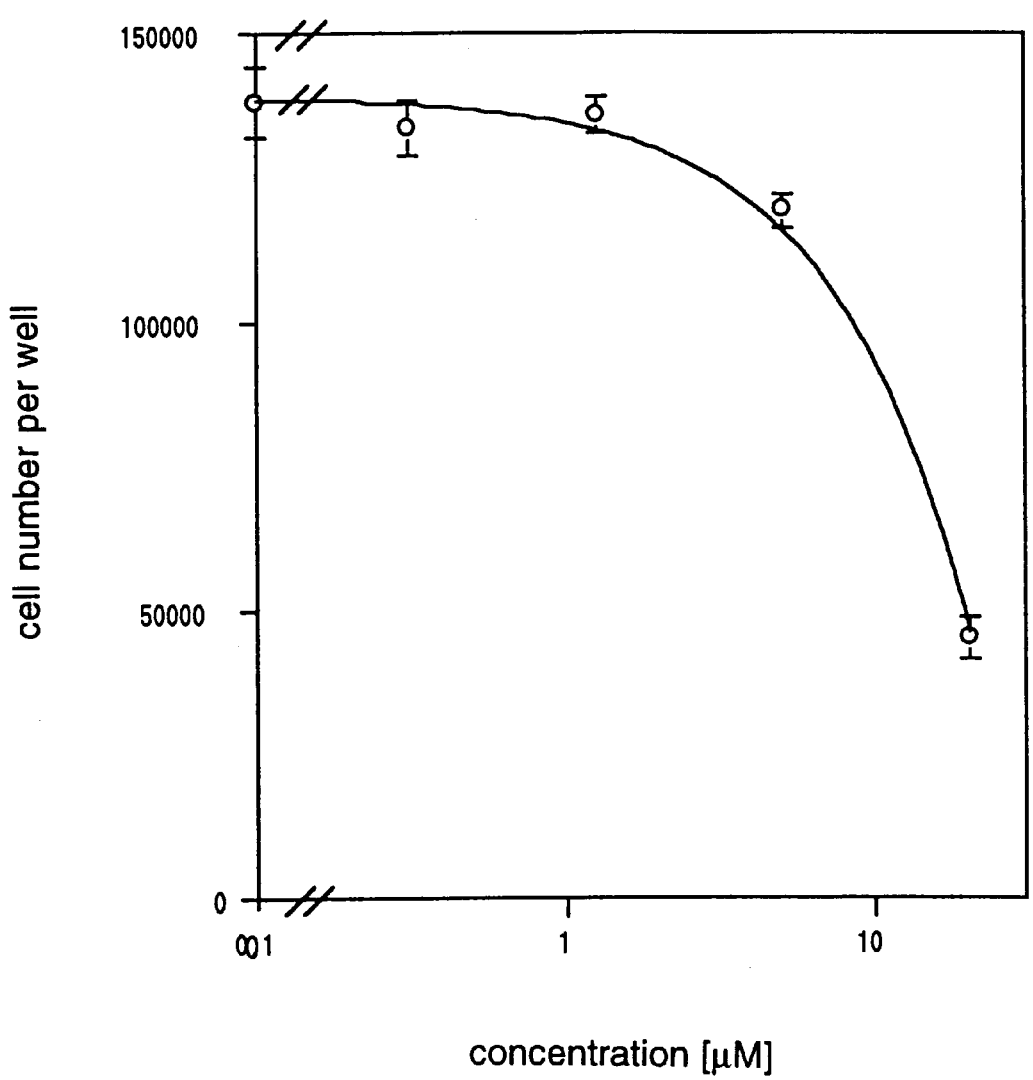
FIG. 3 shows the activity to inhibit growth of smooth muscle cells by the peptide corresponding to the C-terminal of TFPI (Peptide 1) at various concentrations.

The cells suspended in Humedia-SG were inoculated to a 48-well culture plate (manufactured by Iwaki Glass K.K.) at 2,500 cells/well and cultured in $CO_2$ incubator at 37° C. On the next day of inoculation, the culture medium was exchanged with Humedia-SG (0.3 ml/well) containing respective concentration of Peptide 1 and the culture was continued at 37° C. while exchanging the culture medium with the fresh Humedia-SG for every 2 days. Nine days after inoculation, a cell number per well was counted as in Example 2. FIG. 3 shows a mean value and standard deviation of a cell number for each group comprising 4 wells.

It was revealed that Peptide 1 exhibited the significant activity to inhibit growth of smooth muscle cells when it is present at a concentration of about 3 to 5 μM or more in a culture medium. However, it should be noted that the culture medium used in this Example is much abundant in various growth factors, and thus, in case of DME containing 10% FCS as usually used for growing smooth muscle cells, or in case of administration into the living body, Peptide 1 would possibly exert the significant activity to inhibit growth of smooth muscle cells at a lesser amount.

Example 6

Activity to Inhibit Growth of Smooth Muscle Cells by Various Peptides

Figure 4:
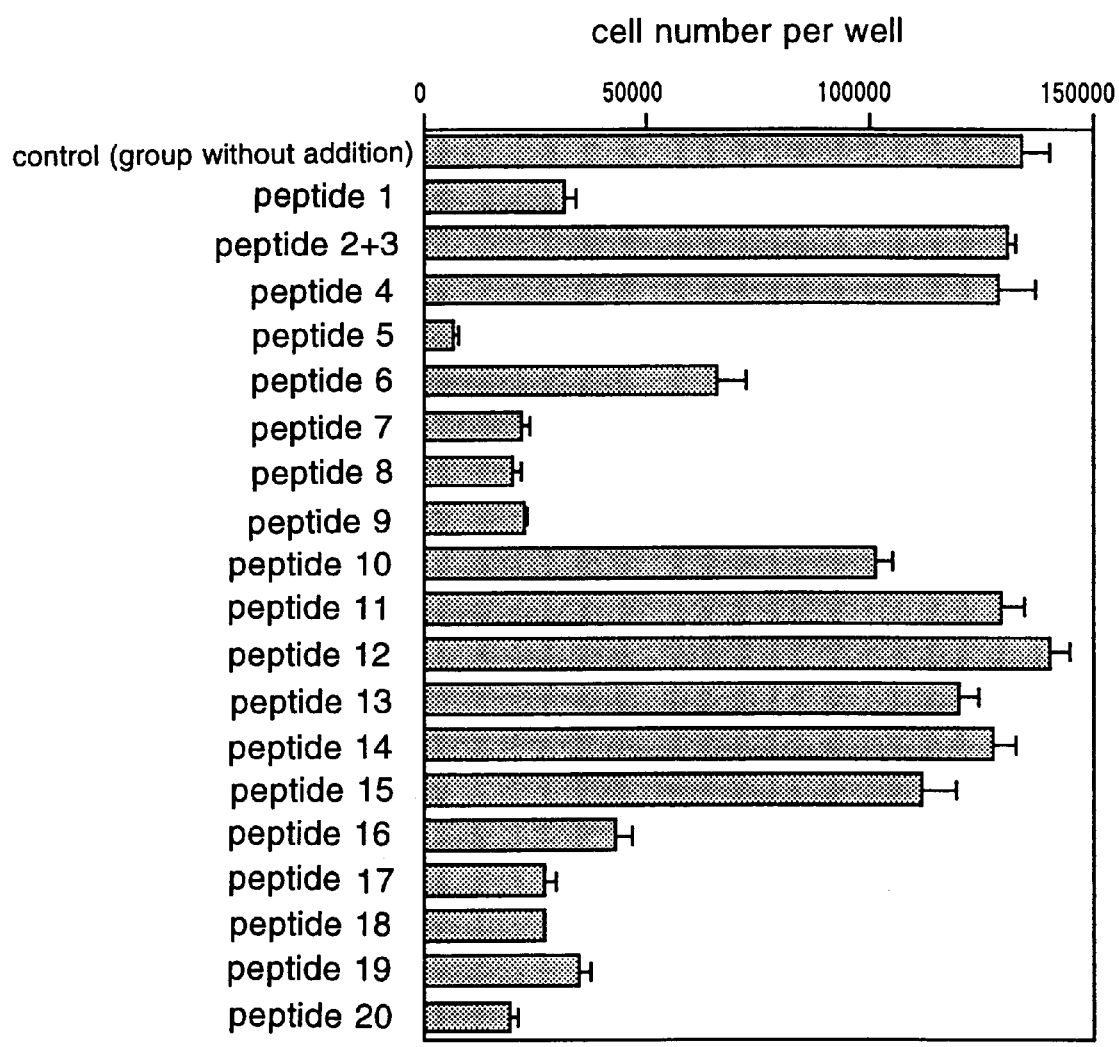
FIG. 4 shows the activity to inhibit growth of smooth muscle cells by various synthetic peptides.

The cells were inoculated as in Example 5. On the next day of inoculation, the culture medium was exchanged with Humedia-SG containing respective peptide prepared in Example 3 at a final concentration of 20 μM and the culture was continued at 37° C. while exchanging the culture medium with the Humedia-SG. Ten days after inoculation, a cell number per well was counted as in Example 2. FIG. 4 shows a mean value and standard deviation of a cell number for each group comprising 4 wells. Every group showed 5% or less of a lethal rate of the cells.

The results shown in FIG. 4 lead to the following conclusion.

(1) Comparison Between Peptide 1 and Peptides 2+3

The Peptides 2+3 are a mixture of an equal amount (each 20 μM) of Peptide 2, which corresponds to eleven amino acid residues in the N-terminal region of Peptide 1, and Peptide 3, which corresponds to twelve amino acid residues in the C-terminal region. Peptide 1 strongly inhibited growth of smooth muscle cells whereas Peptides 2+3 exhibited no activity. It was revealed from this result that both specific amino acid sequences in Peptide 2 and in Peptide 3 should be present in a single molecule so that the activity to inhibit growth of smooth muscle cells is exerted.

(2) Comparison Between Peptide 1 and Peptides 7 to 9

Peptides 7, 8 and 9 are a modified Peptide 1 wherein the four amino acid residues (Ala-Tyr-Glu-Glu (SEQ ID NO:26)) ranging from the 14th amino acid residue Ala to the 17th amino acid residue Glu are either deleted or substituted. Since the activity to inhibit growth of smooth muscle cells as in Peptide 1 was exhibited even after deletion or substitution in this region, it was revealed that thirteen amino acid residues and six amino acid residues in the N- and C-terminal regions, respectively, of Peptide 1, are responsible for the activity to inhibit growth of smooth muscle cells.

(3) Comparison Between Peptide 1 and Peptide 4

Peptide 4 is such that thirteen amino acid residues in the N-terminal region of Peptide 1, being abundant in basic amino acid residues, is placed at the C-terminal while six amino acid residues in the C-terminal region of Peptide 1, comprising many hydrophobic amino acid residues, is placed at the N-terminal. It was revealed that since Peptide 4 exhibited no activity to inhibit growth of smooth muscle cells, placing said region being abundant in basic amino acid residues and said region having many hydrophobic amino acid residues at the N-terminal and the C-terminal, respectively, was essential for exerting the activity.

(4) Comparison Between Peptide 1 and Peptide 10

Peptide 10 is a modified Peptide 1 wherein the N-terminal region being abundant in basic amino acid residues is replaced with a corresponding region having less basic amino acid residues. Specifically, Peptide 10 is a modified Peptide 1 wherein twelve amino acid residues in the N-terminal region are replaced with the heparin binding region of platelet factor IV having an amino acid sequence: LYKKIIKKLLES (Amino acids 1–12 of SEQ ID NO:10).

Peptide 1 comprises nine basic amino acid residues in the N-terminal region of thirteen amino acid residues whereas Peptide 10 comprises only four basic amino acid residues. Although reduction in the number of a basic amino acid residue to four extremely lowers the activity to inhibit growth of smooth muscle cells as compared to Peptide 1, the statistically significant activity still remained as compared to the control group (Student's t-test; $p<0.05$). Thus, it was revealed that at least four among thirteen amino acid residues in the region being abundant in basic amino acid residues should be a basic amino acid for exerting the inhibitory activity.

(5) Comparison Between Peptide 1 and Peptide 6

Peptide 6 is a modified Peptide 1 wherein the hydrophobic amino acid residues Ile, Phe, Val and Met in the C-terminal region consisting of six amino acid residues (Ile-Phe-Val-Lys-Asn-Met (amino acids 18–20 of SEQ ID NO:1)) of Peptide 1 are substituted with another hydrophobic amino acid, leucine (Leu). It was shown that Peptide 6 still exhibited a strong activity to inhibit growth of smooth muscle cells though reduced by about ⅓. This revealed that the hydrophobic amino acid residues in the C-terminal region of the peptide is not limited to those appeared on Peptide 1 but may be any hydrophobic amino acid residue and that the hydrophobic amino acid residues in the C-terminal region play an important role in exerting the activity to inhibit growth of smooth muscle cells.

(6) Comparison Between Peptide 1 and Peptides 11–20

Peptide 20 is a modified Peptide 1 wherein the hydrophobic amino acid Ile is added to the N-terminal of Peptide 1. Since the addition of this one amino acid residue enhanced the activity to inhibit growth of smooth muscle cells as compared to Peptide 1, it is preferable to add at least one hydrophobic amino acid (e.g. Ile) to the N-terminal of the region being abundant in basic amino acid residues for designing peptides having more potent activity to inhibit growth of smooth muscle cells.

Peptides 11–19 are a modified Peptide 20 wherein the C-terminal region of Peptide 20 is deleted to various degrees. Specifically, Peptides 19–14 is a modified Peptide 20 wherein an amino acid residue in the C-terminal region of Peptide 20 is deleted one by one. Peptides 13–11 are a modified Peptide 14 wherein four, six or eight amino acid residues in the C-terminal region of Peptide 14 is deleted, respectively. As a result, it was shown that Peptide 16 wherein four amino acid residues in the C-terminal region were deleted from Peptide 20 maintains strong activity to inhibit growth of smooth muscle cells whereas Peptide 15 wherein five amino acid residues in the C-terminal region were deleted from Peptide 20 almost lost the activity.

It was revealed that (i) from the results obtained in the item (2), the four amino acid residues (Ala-Tyr-Glu-Glu (SEQ ID NO:26)), corresponding to the 14th amino acid residue Ala to the 17th amino acid residue Glu counted from the N-terminal of Peptide 1, do not contribute to the activity to inhibit growth of smooth muscle cells; and that (ii) from the results obtained in the item (5), the hydrophobic amino acid residues in the C-terminal six amino acid sequence of Peptide 1 play an important role in the activity to inhibit growth of smooth muscle cells and thus at least two consecutive, hydrophobic amino acid residues should be present in the C-terminal region for exerting the activity.

(7) Comparison Between Peptide 1 and Peptide 5

Peptide 5 is a modified Peptide 1 wherein the basic amino acid Lys situated at the 3rd position counted from the C-terminal of Peptide 1 is substituted with non-hydrophilic amino acid Gln. This amino acid substitution enhanced the activity of Peptide 1. That is, Lys at the 3rd position counted from the C-terminal of Peptide 1 is preferably substituted with Gln for exerting the excellent activity to inhibit growth of smooth muscle cells.

INDUSTRIAL APPLICABILITY OF THE INVENTION

The peptide of the present invention has the excellent activity to inhibit growth of smooth muscle cells and can be effective as a medicament for preventing and treating pathological conditions associated with growth of smooth muscle cells such as arteriosclerosis, restenosis after angioplasty, luminal stenosis after grafting blood vessel and smooth muscle sarcoma. A pharmaceutical composition comprising the peptide of the present invention is advantageous in the following points:

(i) It can be prepared at low cost in large amount by a chemical synthesis without using human plasma as a starting material or without the need of production by genetic recombination technique. As a result, a risk of pathogen contamination from human plasma or host cell used in the genetic recombination technique is obviated, which allows for production of a quite safe medicament.

(ii) By designing the peptide of the present invention so that it has only the activity to inhibit growth of smooth muscle cells, unnecessary physiological activity or unknown side effect induced by those regions irrelevant to the desired activity is excluded to allow for administration of the peptide at a higher concentration and at a larger amount. For example, such a peptide obviates hemorrhagic side effect which might possibly be induced by administration of full-length TFPI.

(iii) A more potent drug can be prepared by appropriately altering the amino acid sequence of the peptide of the present invention or by using a suitable chemical modification. Furthermore, it is possible to extend an administration route, such as formulation into an orally administrable pharmaceutical composition.

What is claimed is:

1. A peptide which consists of an amino acid sequence selected from the group consisting of SEQ ID NO:5, SEQ ID NO:6, SEQ ID NO:7, SEQ ID NO:8 and SEQ ID NO:9.

2. The peptide of claim 1 which is the amino acid sequence of SEQ ID NO: 5.

3. A process for preventing or treating pathological conditions associated with growth of smooth muscle cells, which comprises administering to a patient in need thereof a peptide having an activity to inhibit growth of smooth muscle cells, wherein said peptide is homologous to a C-terminal region of tissue factor pathway inhibitor (TFPI), said C-terminal region being obtained after removal of a region ranging from the N-terminal to at least Kunitz 3 from TFPI so that said C-terminal region comprises up to thirty seven amino acid residues, wherein said peptide consists of a peptide (A) of an amino acid sequence with thirteen amino acids in length among which more than four amino acids are basic amino acids and a peptide (B) of an amino acid sequence comprising at least two consecutive, hydrophobic amino acid residues, said amino acid sequence being selected from the group consisting of Ile-Phe, Ile-Phe-Val, Ile-Phe-Val-Xaa (SEQ ID NO:23), Ile-Phe-Val-Xaa-Asn (SEO ID NO:24) and Ile-Phe-Val-Xaa-Asn-Met (SEO ID NO:25) in which Xaa is either Lys or Gln, wherein said peptide (B) is linked to the C-terminal of said peptide (A) directly or via four amino acid residues.

4. A process according to claim 3, wherein said pathological condition is restinosis after Percutaneous Transluminal Coronary Angioplasty, atherectomy, laser excision or stent implant.

5. A process according to claim 4, wherein said restinosis is due to Percutaneous Transluminal Coronary Angioplasty.

6. A process according to claim 3, wherein said four amino acid residues consist of Ala-Tyr-Glu-Glu (SEQ ID NO:26), Ala-Tyr-Gln-Gln (amino acids 14–17 of SEQ ID NO:8) or Ser-Phe-Glu-Glu (amino acids 14–17 of SEQ ID NO:9).

7. A process according to claim 3, wherein said peptide having an activity to inhibit growth of smooth muscle cells consists of an amino acid sequence selected from the group consisting of SEQ ID NO:5, SEQ ID NO:6, SEQ ID NO:7, SEQ ID NO:8, SEQ ID NO:9, SEQ ID NO:16, SEQ ID NO:17, SEQ ID NO:18 and SEQ ID NO:19.

8. The process of claim 3, wherein the basic amino acid residue in the peptide (A) is selected from the group consisting of lysine, arginine and histidine.

9. The process of claim 3, wherein the peptide (A) consists of a sequence of 13 amino acid residues, among which 9 amino acid residues are basic amino acids.

10. The process of claim 3, wherein the peptide (A) consists of the following sequence of 13 amino acid residues: Ba1-Xa1-Ba2-Ba3-Ba4-Ba5-Ba6-Ba7-Xa2-Ba8-Xa3-Ba9-Xa4 (SEO ID NO:21) in which Ba1, Ba2, Ba3, Ba4, Ba5, Ba6, Ba7, Ba8 and Ba9 are basic amino acids each selected from the group consisting of Lys, Arg and His; and wherein Xa1, Xa2, Xa3 and Xa4 are any amino acid.

11. The process of claim 10, wherein said sequence of thirteen amino acid residues consists of a sequence: Lys-Xa1-Lys-Arg-Lys-Arg-Lys-Lys-Xa2-Arg-Xa3-Lys-Xa4 (SEQ ID NO:22).

12. The process of claim 11, wherein said sequence of thirteen amino acid residues consists of a sequence: Lys-Thr-Lys-Arg-Lys-Arg-Lys-Lys-Gln-Arg-Val-Lys-Ile (amino acids 1–13 of SEQ ID NO:1).

13. The process of claim 3, wherein said at least two consecutive, hydrophobic amino acid residues in the peptide (B) comprise an amino acid sequence: Ile-Phe.

14. The process of claim 3, wherein said at least two consecutive, hydrophobic amino acid residues in the peptide (B) comprise an amino acid sequence: Ile-Phe-Val.

15. The process of claim 3, wherein the peptide (B) consist of an amino acid sequence: Ile-Phe-Val-Xaa (SEQ ID NO:23).

16. The process of claim 3, wherein the peptide (B) comprises an amino acid sequence: Ile-Phe-Val-Xaa-Asn (SEQ ID NO:24).

17. The process of claim 3, wherein the peptide (B) consist of an amino acid sequence: Ile-Phe-Val-Xaa-Asn-Met (SEQ ID NO:25).

18. The process of claim 15, wherein said Xaa is Lys.

19. The process of claim 15, wherein said Xaa is Gln.

* * * * *

SEQUENCE LISTING

<160> NUMBER OF SEQ ID NOS: 26

<210> SEQ ID NO 1
<211> LENGTH: 23
<212> TYPE: PRT
<213> ORGANISM: Human Tissue Factor Pathway Inhibitor

```
<400> SEQUENCE: 1

Lys Thr Lys Arg Lys Arg Lys Lys Gln Arg Val Lys Ile Ala Tyr Glu
 1               5                  10                  15

Glu Ile Phe Val Lys Asn Met
            20

<210> SEQ ID NO 2
<211> LENGTH: 11
<212> TYPE: PRT
<213> ORGANISM: Human Tissue Factor Pathway Inhibitor

<400> SEQUENCE: 2

Lys Thr Lys Arg Lys Arg Lys Lys Gln Arg Val
 1               5                  10

<210> SEQ ID NO 3
<211> LENGTH: 12
<212> TYPE: PRT
<213> ORGANISM: Human Tissue Factor Pathway Inhibitor

<400> SEQUENCE: 3

Lys Ile Ala Tyr Glu Glu Ile Phe Val Lys Asn Met
 1               5                  10

<210> SEQ ID NO 4
<211> LENGTH: 23
<212> TYPE: PRT
<213> ORGANISM: Human Tissue Factor Pathway Inhibitor

<400> SEQUENCE: 4

Ile Phe Val Lys Asn Met Ala Tyr Glu Glu Lys Thr Lys Arg Lys Arg
 1               5                  10                  15

Lys Lys Gln Arg Val Lys Ile
            20

<210> SEQ ID NO 5
<211> LENGTH: 23
<212> TYPE: PRT
<213> ORGANISM: Human Tissue Factor Pathway Inhibitor

<400> SEQUENCE: 5

Lys Thr Lys Arg Lys Arg Lys Lys Gln Arg Val Lys Ile Ala Tyr Glu
 1               5                  10                  15

Glu Ile Phe Val Gln Asn Met
            20

<210> SEQ ID NO 6
<211> LENGTH: 23
<212> TYPE: PRT
<213> ORGANISM: Human Tissue Factor Pathway Inhibitor

<400> SEQUENCE: 6

Lys Thr Lys Arg Lys Arg Lys Lys Gln Arg Val Lys Ile Ala Tyr Glu
 1               5                  10                  15

Glu Leu Leu Leu Lys Asn Leu
            20

<210> SEQ ID NO 7
<211> LENGTH: 19
<212> TYPE: PRT
<213> ORGANISM: Human Tissue Factor Pathway Inhibitor

<400> SEQUENCE: 7
```

```
Lys Thr Lys Arg Lys Arg Lys Lys Gln Arg Val Lys Ile Ile Phe Val
 1               5                  10                  15

Lys Asn Met
```

<210> SEQ ID NO 8
<211> LENGTH: 23
<212> TYPE: PRT
<213> ORGANISM: Human Tissue Factor Pathway Inhibitor

<400> SEQUENCE: 8

```
Lys Thr Lys Arg Lys Arg Lys Lys Gln Arg Val Lys Ile Ala Tyr Gln
 1               5                  10                  15

Gln Ile Phe Val Lys Asn Met
            20
```

<210> SEQ ID NO 9
<211> LENGTH: 23
<212> TYPE: PRT
<213> ORGANISM: Human Tissue Factor Pathway Inhibitor

<400> SEQUENCE: 9

```
Lys Thr Lys Arg Lys Arg Lys Lys Gln Arg Val Lys Ile Ser Phe Glu
 1               5                  10                  15

Glu Ile Phe Val Lys Asn Met
            20
```

<210> SEQ ID NO 10
<211> LENGTH: 23
<212> TYPE: PRT
<213> ORGANISM: Human Tissue Factor Pathway Inhibitor

<400> SEQUENCE: 10

```
Leu Tyr Lys Lys Ile Ile Lys Lys Leu Leu Glu Ser Ile Ala Tyr Glu
 1               5                  10                  15

Glu Ile Phe Val Lys Asn Met
            20
```

<210> SEQ ID NO 11
<211> LENGTH: 10
<212> TYPE: PRT
<213> ORGANISM: Human Tissue Factor Pathway Inhibitor

<400> SEQUENCE: 11

```
Ile Lys Thr Lys Arg Lys Arg Lys Lys Gln
 1               5                  10
```

<210> SEQ ID NO 12
<211> LENGTH: 12
<212> TYPE: PRT
<213> ORGANISM: Human Tissue Factor Pathway Inhibitor

<400> SEQUENCE: 12

```
Ile Lys Thr Lys Arg Lys Arg Lys Lys Gln Arg Val
 1               5                  10
```

<210> SEQ ID NO 13
<211> LENGTH: 14
<212> TYPE: PRT
<213> ORGANISM: Human Tissue Factor Pathway Inhibitor

<400> SEQUENCE: 13

```
Ile Lys Thr Lys Arg Lys Arg Lys Lys Gln Arg Val Lys Ile
```

-continued

```
         1               5                  10
```

<210> SEQ ID NO 14
<211> LENGTH: 18
<212> TYPE: PRT
<213> ORGANISM: Human Tissue Factor Pathway Inhibitor

<400> SEQUENCE: 14

Ile Lys Thr Lys Arg Lys Arg Lys Lys Gln Arg Val Lys Ile Ala Tyr
 1               5                  10                  15

Glu Glu

<210> SEQ ID NO 15
<211> LENGTH: 19
<212> TYPE: PRT
<213> ORGANISM: Human Tissue Factor Pathway Inhibitor

<400> SEQUENCE: 15

Ile Lys Thr Lys Arg Lys Arg Lys Lys Gln Arg Val Lys Ile Ala Tyr
 1               5                  10                  15

Glu Glu Ile

<210> SEQ ID NO 16
<211> LENGTH: 20
<212> TYPE: PRT
<213> ORGANISM: Human Tissue Factor Pathway Inhibitor

<400> SEQUENCE: 16

Ile Lys Thr Lys Arg Lys Arg Lys Lys Gln Arg Val Lys Ile Ala Tyr
 1               5                  10                  15

Glu Glu Ile Phe
            20

<210> SEQ ID NO 17
<211> LENGTH: 21
<212> TYPE: PRT
<213> ORGANISM: Human Tissue Factor Pathway Inhibitor

<400> SEQUENCE: 17

Ile Lys Thr Lys Arg Lys Arg Lys Lys Gln Arg Val Lys Ile Ala Tyr
 1               5                  10                  15

Glu Glu Ile Phe Val
            20

<210> SEQ ID NO 18
<211> LENGTH: 22
<212> TYPE: PRT
<213> ORGANISM: Human Tissue Factor Pathway Inhibitor

<400> SEQUENCE: 18

Ile Lys Thr Lys Arg Lys Arg Lys Lys Gln Arg Val Lys Ile Ala Tyr
 1               5                  10                  15

Glu Glu Ile Phe Val Lys
            20

<210> SEQ ID NO 19
<211> LENGTH: 23
<212> TYPE: PRT
<213> ORGANISM: Human Tissue Factor Pathway Inhibitor

<400> SEQUENCE: 19

Ile Lys Thr Lys Arg Lys Arg Lys Lys Gln Arg Val Lys Ile Ala Tyr

-continued

```
                1               5              10              15

Glu Glu Ile Phe Val Lys Asn
                20

<210> SEQ ID NO 20
<211> LENGTH: 24
<212> TYPE: PRT
<213> ORGANISM: Human Tissue Factor Pathway Inhibitor

<400> SEQUENCE: 20

Ile Lys Thr Lys Arg Lys Arg Lys Gln Arg Val Lys Ile Ala Tyr
 1               5              10                      15

Glu Glu Ile Phe Val Lys Asn Met
                20

<210> SEQ ID NO 21
<211> LENGTH: 13
<212> TYPE: PRT
<213> ORGANISM: Human Tissue Factor Pathway Inhibitor
<220> FEATURE:
<223> OTHER INFORMATION: Xaa in positions 1, 3, 4, 5, 6, 7, 8, 10
      and 13 are basic amino acids selected from the group of
      Lys, Arg or His.  Xaa in positions 2, 9, 11 and 12
      are any amino acid.

<400> SEQUENCE: 21

Xaa Xaa Xaa Xaa Xaa Xaa Xaa Xaa Xaa Xaa Xaa Xaa Xaa
 1               5              10

<210> SEQ ID NO 22
<211> LENGTH: 13
<212> TYPE: PRT
<213> ORGANISM: Human Tissue Factor Pathway Inhibitor
<220> FEATURE:
<223> OTHER INFORMATION: Xaa in positions 2, 9, 11 and 13 are any amino
      acid.

<400> SEQUENCE: 22

Lys Xaa Lys Arg Lys Arg Lys Lys Xaa Arg Xaa Lys Xaa
 1               5              10

<210> SEQ ID NO 23
<211> LENGTH: 4
<212> TYPE: PRT
<213> ORGANISM: Human Tissue Factor Pathway Inhibitor
<220> FEATURE:
<223> OTHER INFORMATION: Xaa in position 4 is either Lys or Gln.

<400> SEQUENCE: 23

Ile Phe Val Xaa
 1

<210> SEQ ID NO 24
<211> LENGTH: 5
<212> TYPE: PRT
<213> ORGANISM: Human Tissue Factor Pathway Inhibitor
<220> FEATURE:
<223> OTHER INFORMATION: Xaa in position 4 is either Lys or Gln.

<400> SEQUENCE: 24

Ile Phe Val Xaa Asn
 1               5

<210> SEQ ID NO 25
<211> LENGTH: 6
<212> TYPE: PRT
```

-continued

```
<213> ORGANISM: Human Tissue Factor Pathway Inhibitor
<220> FEATURE:
<223> OTHER INFORMATION: Xaa in position 4 is either Lys or Gln.

<400> SEQUENCE: 25

Ile Phe Val Xaa Asn Met
  1               5

<210> SEQ ID NO 26
<211> LENGTH: 4
<212> TYPE: PRT
<213> ORGANISM: Human Tissue Factor Pathway Inhibitor

<400> SEQUENCE: 26

Ala Tyr Glu Glu
```